United States Patent

Yoshida

(10) Patent No.: US 8,829,180 B2
(45) Date of Patent: Sep. 9, 2014

(54) METHOD OF PURIFYING A LOW MOLECULAR WEIGHT HYALURONIC ACID OR CATIONIZED HYALURONIC ACID VIA PRECIPITATION FROM AQUEOUS SOLUTION BY ADDITION OF ALCOHOL OR ACETONE FOLLOWED BY PH ADJUSTMENT

(75) Inventor: Takushi Yoshida, Kunitachi (JP)

(73) Assignee: Kewpie Corporation (JP)

(*) Notice: Subject to any disclaimer, the term of this patent is extended or adjusted under 35 U.S.C. 154(b) by 0 days.

(21) Appl. No.: 13/388,010

(22) PCT Filed: Dec. 1, 2010

(86) PCT No.: PCT/JP2010/071437
§ 371 (c)(1),
(2), (4) Date: Jan. 30, 2012

(87) PCT Pub. No.: WO2011/070948
PCT Pub. Date: Jun. 16, 2011

(65) Prior Publication Data
US 2012/0130063 A1   May 24, 2012

(30) Foreign Application Priority Data
Dec. 8, 2009 (JP) .................................. 2009-278259

(51) Int. Cl.
*C08B 37/00* (2006.01)
*A61K 8/73* (2006.01)
*A61K 31/728* (2006.01)
*A23L 1/30* (2006.01)

(52) U.S. Cl.
CPC ............. *C08B 37/0069* (2013.01); *A61K 8/735* (2013.01); *A61K 31/728* (2013.01); *A23L 1/30* (2013.01)
USPC .......................................................... 536/53

(58) Field of Classification Search
CPC .. C08B 37/0069; A61K 8/735; A61K 31/728; A23L 1/30
See application file for complete search history.

(56) References Cited

U.S. PATENT DOCUMENTS

| 7,196,180 | B2 * | 3/2007 | Aeschlimann et al. ...... 536/18.7 |
| 2007/0224277 | A1 * | 9/2007 | Borbely et al. ............... 424/489 |
| 2009/0215719 | A1 | 8/2009 | Yoshida |
| 2010/0197904 | A1 | 8/2010 | Asaoka et al. |

FOREIGN PATENT DOCUMENTS

| EP | 1865002 A1 | 12/2007 |
| JP | 63-057602 A | 3/1988 |
| JP | 1-266102 A | 10/1989 |
| JP | 5-077681 B | 10/1993 |
| JP | 5-255045 A | 10/1993 |
| JP | 2006-36666 A | 2/2006 |
| JP | 2006-265287 A | 10/2006 |
| JP | 2007-186689 A | 7/2007 |
| JP | 2008-179710 A | 8/2008 |
| JP | 2009-155486 A | 7/2009 |
| WO | WO-2006-101030 A1 | 9/2006 |
| WO | WO-2008-133267 A1 | 11/2008 |

OTHER PUBLICATIONS

"type" In: American Heritage Medical Dictionary, Houghton Mifflin Co., 2007. [retrieved on Apr. 22, 2013]. Retrieved from: http://www.credoreference.com/entry/hmmedicaldict/type.*
Ripin and Evans, pKa Table, Nov. 2005, retrieved from: http://www2.lsdiv.harvard.edu/labs/evans/pdf/evans_pKa_table.pdf on Dec. 16, 2013.*
Laurent, Torvard. T., et al., "Fractionation of Hyaluronic Acid", Biochemina et Biophysica Acta., 42, 476-485 (1960) (in English).
Yomota, Chikako, "Evaluation of Molecular Weights of Hyaluronate Preparations by Multi-Angle laser Light Scattering", Bull. Natl. Inst. Health Sci., 121, 030-033 (2003) (with English Abstract).
English translation of International Preliminary Report on Patentability for Application No. PCT/JP2010/071437 issued Jul. 10, 2012 (5 pages).
Supplementary Extended European Search Report for Application No. EP 10 835 870.6 dated Sep. 17, 2013 (6 pages).
Raja, Rampyari H. et al., "Preparation of Alkylamine and $^{125}$I-Radiolabeled Derivatives of Hyaluronic Acid Uniquely Modified at the Reducing End", Division of Biochemistry, Department of Human Biological Chemistry and Genetics, University of Texas Medical Branch, Galveston, TX 77550, Oct. 31, 1983, pp. 168-177.

* cited by examiner

Primary Examiner — Shaojia Anna Jiang
Assistant Examiner — Dale R Miller
(74) Attorney, Agent, or Firm — Harness, Dickey & Pierce, P.L.C.

(57) ABSTRACT

Provided a method of producing a purified hyaluronic acid type which comprises adding a water-soluble organic medium to a solution which comprises a hyaluronic acid type having an average molecular weight of 400 to 100,000 and has a pH of 3 or less to obtain a suspension, and adjusting a pH of the suspension in a range of 3.5 to 8 to precipitate a purified hyaluronic acid type.

2 Claims, No Drawings

METHOD OF PURIFYING A LOW MOLECULAR WEIGHT HYALURONIC ACID OR CATIONIZED HYALURONIC ACID VIA PRECIPITATION FROM AQUEOUS SOLUTION BY ADDITION OF ALCOHOL OR ACETONE FOLLOWED BY PH ADJUSTMENT

CROSS-REFERENCE TO RELATED APPLICATIONS

This application is a U.S. National Stage Application of International Application No. PCT/JP2010/071437, filed on Dec. 1, 2010 and published in Japanese as WO/2011/070948 on Jun. 16, 2011. This application claims the benefit of Japanese Application No. 2009-278259, filed on Dec. 8, 2009. The entire disclosures of the above applications are incorporated herein by reference.

TECHNICAL FIELD

The invention relates to a method of producing a purified hyaluronic acid type.

BACKGROUND ART

Hyaluronic acid presents widely in living tissues such as cockscombs, umbilical cords, skin, cartilages, vitreous bodies, joint fluid, and is widely used as a component of cosmetics, medical supplies, and foodstuffs, for example. Also, in recent years, approaches to utilization of chemically-modified hyaluronic acid and low-molecular-weight hyaluronic acid as a component of cosmetics, medical supplies, and foodstuffs have been made. For example, WO 2008/133267 describes cationized hyaluronic acid and a method of producing the same. Also, JP-B-5-77681 describes a method for reducing a molecular weight of hyaluronic acid.

WO2008/133267 describes the method of producing the cationized hyaluronic acid, which comprises reacting hyaluronic acid (average molecular weight: 2,000,000) with a cationizing agent in a basic aqueous medium, dissolving a solid obtained by decantation for removing a liquid to a saline solution, then adding an alcohol to the solution to obtain a precipitate, separating the precipitate by filtration, then washing the precipitate with ethanol for purification, and then drying the separated precipitate. Thus, in order to obtain hyaluronic acid or chemically-modified hyaluronic acid from a process solution the hyaluronic acid or the chemically-modified hyaluronic acid is generally precipitated by adding ethanol to the process solution. However, it is not easy for low-molecular-weight hyaluronic acid (for example, hyaluronic acid having an average molecular weight of 100,000 or less) to precipitate by adding ethanol to the process solution merely, and thus a low recovery rate has been a problem.

Additionally, JP-B-5-77681 describes methods of degrading hyaluronic acid in an acidic aqueous solution, then precipitating hyaluronic acid by adding ethanol to the solution, then separating the precipitate by filtration, and washing each precipitate with ethanol for purification. However, in this method, the recovery rate of the hyaluronic acid is low, and thus more efficient method of producing a low-molecular-weight hyaluronic acid has been desired.

DISCLOSURE OF THE INVENTION

The invention provides a method of producing a purified hyaluronic acid type, which can obtain a purified hyaluronic acid type having a low-molecular-weight at a high recovery rate.

According to one aspect of the invention, there is provided a method of producing a purified hyaluronic acid type comprising:

adding a water-soluble organic medium to a solution which comprises a hyaluronic acid type having an average molecular weight of 400 to 100,000 and has a pH of 3 or less to obtain a suspension; and adjusting a pH of the suspension in a range of 3.5 to 8 to precipitate a purified hyaluronic acid type.

In the above method of producing the purified hyaluronic acid type, a pH of the solution before adding the water-soluble organic medium may be 2 or less.

By the above method of producing the purified hyaluronic acid type which comprises adding a water-soluble organic medium to a solution which comprises a purified hyaluronic acid type having an average molecular weight of 400 to 100,000 and has a pH of 3 or less to obtain a suspension and adjusting a pH of the suspension in a range of 3.5 to 8 to precipitate a purified hyaluronic acid type, the purified hyaluronic acid type having a low-molecular-weight can be obtained at a high recovery rate.

MODES FOR CARRYING OUT THE INVENTION

A method of producing a purified hyaluronic acid type according to one embodiment of the invention is described in detail below. Furthermore, in the invention, "%5" indicates "mass %" and "part" indicates "mass part".

1. Method Of Producing A Purified Hyaluronic Acid Type

A method of producing a purified hyaluronic acid type according to this embodiment comprises adding a water-soluble organic medium to a solution which comprises a purified hyaluronic acid type having an average molecular weight of 400 to 100,000 and has a pH of 3 or less to obtain a suspension, and adjusting a pH of the suspension in a range of 3.5 to 8 to precipitate a purified hyaluronic acid type.

The method of producing the purified hyaluronic acid type according to this embodiment can be performed after processing a hyaluronic acid solution. This can separate the purified hyaluronic acid type from other components in the process solution by precipitation.

Processing the hyaluronic acid solution may be for example, extracting hyaluronic acid and/or its salt (for example, extraction from natural products), producing hyaluronic acid and/or its salt (for example, cultivation, chemical synthesis, enzymatic synthesis), reducing a molecular weight of hyaluronic acid and/or its salt (for example, acidic process, basic process, enzymatic process (for example, process with hyaluronidase), high-pressure process, high-temperature process, mechanical shear process, electron beam irradiation process), and chemical modification processing of hyaluronic acid and/or its salt (for example, chemical modification of a functional group contained in hyaluronic acid and/or its salt). Specifically, in terms of workability, the reducing the molecular weight of hyaluronic acid and/or its salt is preferably the acidic process of hyaluronic acid since the pH of the solution comprising the hyaluronic acid type in obtaining the suspension according to the invention is 3 or less.

Alternatively, the method of producing the purified hyaluronic acid type according to this embodiment may be demonstrated for the purpose of reducing impurities existing in hyaluronic acid and/or its salt.

The term "purified hyaluronic acid type" used in the invention refers to a hyaluronic acid type having a content of the hyaluronic acid type of 90% or more (preferably 93% or more, more preferably 95% or more). Also, the term "content of the hyaluronic acid type" used in the invention refers to a value which is calculated from a quantitative value of glucuronic acid measured by carbazole-sulfuric acid reaction described hereinafter.

The average molecular weight of the purified hyaluronic acid type is preferably 400 to 100,000, and more preferably 400 to 50,000, still more preferably 400 to 10,000.

The method of producing the purified hyaluronic acid type according to this embodiment can achieve a high recovery rate of the purified hyaluronic acid type, and can easily enhance the purity of the purified hyaluronic acid type.

1.1. Raw Material

A raw material in the method of producing the purified hyaluronic acid type according to this embodiment is preferably a hyaluronic acid type having the average molecular weight of 400 to 100,000 (more preferably 400 to 50,000, and still more preferably 400 to 10,000). The term "raw material" used in the invention refers to a hyaluronic acid type which is object of the method of producing the purified hyaluronic acid type according to this embodiment. Therefore, when the method of producing the purified hyaluronic acid type according to this embodiment is performed after processing the hyaluronic acid solution, an average molecular weight of the raw material refers to an average molecular weight of the hyaluronic acid type after processing the hyaluronic acid solution, for example. Accordingly, for example, when the processing the hyaluronic acid solution is performed for reducing the molecular weight, the average molecular weight of the hyaluronic acid type before reducing the molecular weight may be more than 100,000 (for example, 400 to 3,000,000).

When the average molecular weight of the hyaluronic acid type as a raw material is more than 100,000, gelation may occur at the time that the water-soluble organic medium is added to the solution, the pH of which is adjusted to 3 or less, and separation between suspension phase and supernatant phase may not occur.

The term "hyaluronic acid" used in the invention refers to a polysaccharide including at least one repeating constituent unit formed of a glucuronic acid and a N-acetylglucosamine. Also, the term "hyaluronic acid type" is a concept that includes hyaluronic acid, hyaluronic acid derivative, and salts thereof.

The term "hyaluronic acid derivative" used in the invention refers to a compound such that a functional group (for example, a hydroxyl group, a carboxyl group, an amide group) contained in hyaluronic acid is modified, and examples of the hyaluronic acid derivative are a cationized hyaluronic acid, an acylated hyaluronic acid, an acetylated hyaluronic acid, and the like. Also, "a salt of hyaluronic acid or a salt of hyaluronic acid derivative" is not particularly limited, but preferably a salt being acceptable for food or pharmaceutically acceptable salt, for example, a sodium salt, a potassium salt, a calcium salt, a zinc salt, a magnesium salt, an ammonium salt, and the like.

Hyaluronic acid is basically disaccharide or polysaccharide, which comprises at least one disaccharide unit combining a C-1 position of a beta-D-glucuronic acid and a C-3 position of a beta-D-N-acetyl-glucosamine, and basically composes a beta-D-glucuronic acid and a beta-D-N-acetyl-glucosamine and has more than one of the disaccharide units. The disaccharide or polysaccharide may be an unsaturated sugar, and an example of the unsaturated sugar is a sugar having a non-reducing end, typically, a sugar having a unsaturated bond between a C-4 position and a C-5 position of a glucuronic acid.

Hyaluronic acid and/or its salt, which is a raw material, may be an extract obtained by extraction from natural products such as animals (for example, living tissues such as cockscombs, umbilical cords, skin, joint fluid), or a culture obtained by culturing microorganisms or animal cells (for example, a fermentation method using Streptococcus microorganism, and the like), a chemical synthetic, or an enzymatic synthetic can be used.

1.1.1. Average Molecular Weight

The average molecular weight of the (purified) hyaluronic acid type is a value measured by the following method.

Specifically, about 0.05 g of the (purified) hyaluronic acid type is weighed, and dissolved in a 0.2 mol/l sodium chloride solution to prepare a 100 mL of the resulting solution. A 0.2 mol/l sodium chloride solution is added to 8 mL, 12 mL, or 16 mL of the resulting solution to prepare each of the total amounts of 20 mL solutions.

The each 20 mL solution and the resulting solution are used as sample solutions. The specific viscosity of each of the sample solutions and a 0.2 mol/l sodium chloride solution are measured at 30.0+−0.1° C. by the viscosity measurement method (first method (capillary viscosity measurement method)) of the general tests of Japanese Pharmacopoeia (14th edition) (see expression (1)), and the reduced viscosity at each concentration is calculated (see expression (2)). The reduced viscosity (vertical axis) and the dry matter concentration (g/100 mL) (horizontal axis) are plotted on a graph, and the limiting viscosity is calculated from the intersection point of a straight line that connects each point and the vertical axis. The limiting viscosity thus calculated is substituted into the Laurent's formula (expression (3)) to calculate the average molecular weight (Torvard C Laurent, Marion Ryan, and Adolph Pietruszkiewicz, "Fractionation of hyaluronic Acid", Biochemina et Biophysica Acta., 42, 476-485(1960), and Chikako Yomota, "Evaluation of Molecular Weights of Hyaluronate Preparations by Multi-Angle Laser Light Scattering", Bull. Natl. Inst. Health Sci., 121, 030-033(2003)).

$$\text{Specific viscosity} = [(\text{falling time of sample solution})/(\text{falling time of 0.2 mol/l sodium chloride solution})] - 1 \qquad (1)$$

$$\text{Reduced viscosity (dL/g)} = \text{specific viscosity}/(\text{dry matter concentration (g/100 mL)}) \qquad (2)$$

$$\text{Limiting viscosity (dL/g)} = 3.6 \times 10^{-4} M^{0.78} \qquad (3)$$

M: average molecular weight

1.1.2. Content of Hyaluronic Acid Type

In the (purified) hyaluronic acid type, the content of the hyaluronic acid type is an index for purity of the (purified) hyaluronic acid type, and as the content of the hyaluronic acid type is higher, the purity of the (purified) hyaluronic acid type is higher.

The content of the (purified) hyaluronic acid type used in the invention refers to a value which is calculated from a quantitative value of glucuronic acid measured by carbazole-sulfuric acid reaction (see Japanese Pharmacopoeia, for example).

Carbazole-sulfuric acid reaction is a method of adding an aqueous solution of hyaluronic acid to a sodium boroate-sulfuric acid solution to immingle the both solutions, degrading the hyaluronic acid while heating, then cooling the obtained solution, adding a carbazole-ethanol solution to the obtained solution to immingle the both solutions, heating and then cooling the immingled solution, and measuring an absorbance (530nm) of the resulting solution as a sample. The same process is performed with D-glucuronolactone, a calibration curve for D-glucuronolactone is formed to calculate a value in terms of D-glucuronolactone, and then a quantitative value of glucuronic acid is calculated by multiplying the value in terms of D-glucuronolactone by 1.102. The content of the hyaluronic acid type is calculated by multiplying the obtained quantitative value of glucuronic acid by (the molecular weight of the hyaluronic acid type/the molecular weight of glucuronic acid).

1.2. Obtaining Suspension

According to the method of producing the purified hyaluronic acid type according to this embodiment, by adding the water-soluble organic medium to the solution which has a pH of 3 or less and comprises the hyaluronic acid type having the average molecular weight of 100,000 or less and being a raw material, the suspension is obtained.

"Suspension" used in the invention refers to a mixture such that solid particles are dispersed in liquid. For example, the suspension may be opaque liquid in which solids are dispersed, or suspension phase may separate from supernatant phase in the suspension. Suspension phase preferably separates from supernatant phase since it is easier for the purified hyaluronic acid type to precipitate in the subsequent steps.

The solvent used for the solution comprising the hyaluronic acid type which is a raw material is preferably water. Also, the solution comprising the hyaluronic acid type which is a raw material may comprise an inorganic salt such as sodium chloride of 2% or less (preferably, 1% or less), more preferably, the concentration of the inorganic salt in the solution is less than 1%.

The concentration of the hyaluronic acid type in the solution comprising hyaluronic acid type which is a raw material is not particularly limited, preferably 0.1 to 30%, more preferably 1 to 10%, in terms of enhanced recovery efficiency.

In the process of obtaining the suspension, the additive amount of the water-soluble organic medium may be minimum amounts required for changing a solution to a suspension, or more. Examples of the water-soluble organic medium are, an alcohol medium such as methanol, ethanol, 1-propanol, 2-propanol, a ketone medium such as acetone, methyl ethyl ketone, tetrahydrofuran, acetonitrile, and the like, and these media may be used either individually or in combination, and specifically, the water-soluble organic medium is preferably ethanol.

The additive amount of the water-soluble organic medium is preferably one part or more for one part of the solution comprising the hyaluronic acid type, more preferably 1.5 to 50 parts, still more preferably 1.5 to 20 parts. In this instance, when the additive amount of the water-soluble organic medium is less than one part for one part of the solution comprising the hyaluronic acid type, it is a long time before suspension is generated.

Also, in the process of obtaining the suspension, a pH of the solution before adding the water-soluble organic medium is 3 or less, preferably 0.1 to 2.5, more preferably 0.1 to 2. When the pH of the solution before adding the water-soluble organic medium is more than 3, it is a long time before suspension is generated when the water-soluble organic medium is added, therefore, it is a long time before precipitation of the purified hyaluronic acid type occurs when the pH of the solution is adjusted in a range of 3.5 to 8 in the subsequent process. Alternatively, it may be occasionally undesirable in the case that the pH of the solution before adding the water-soluble organic medium is too low, since a large amount of salt is generated at the time of adjusting the pH of the solution in a range of 3.5 to 8 in the subsequent process.

1.3. Precipitating Hyaluronic Acid Type

According to the method of producing the purified hyaluronic acid type according to this embodiment, the purified hyaluronic acid type is precipitated by adjusting the pH of the suspension in a range of 3.5 to 8. In this instance, when the pH of the suspension is out of range of 3.5 to 8, it is difficult to precipitate the purified hyaluronic acid type. Also, in terms of accomplishment of higher recovery rate, it is preferable to adjust the pH of the suspension in a range of 4 to 7, more preferably, in a range of 4 to 6.

2. Example

The invention is further described below by way of examples. Note that the invention is not limited to the following examples.

2.1. Test Method

In these examples, the average molecular weight of the (purified) hyaluronic acid type was measured by the method explained in the embodiment described above. The content of the (purified) hyaluronic acid type was also calculated from a quantitative value of glucuronic acid by carbazole-sulfuric acid reaction.

2.2. Example 1

Hydrochloric acid was added to two liters of water to adjust the pH of the process solution to 0.3, and the process solution was heated until the temperature of the process solution reached at 70° C. After the temperature of the process solution reached at 70° C., 100 g of hyaluronic acid (average molecular weight: 300,000, manufactured by Kewpie Corporation) was added to the process solution, and then acid decomposition was performed for two hours. Next, the reaction solution was cooled to ambient temperature, and then five liters of ethanol was added little by little to the reaction solution to separate suspension phase from supernatant phase. Further, the pH of the reaction solution was adjusted to 5.0 with sodium hydrate to precipitate the hyaluronic acid, and the precipitate was collected by filtration and was washed three times with 500 mL of 80% (v/v) ethanol. The obtained precipitate was dried in a vacuum at 60° C. to obtain a purified hyaluronic acid.

The average molecular weight of the purified hyaluronic acid obtained in Example 1 was 8,000, and the content of hyaluronic acid in the purified hyaluronic acid was 95.4%. Also, the pH of the process solution before adding ethanol was 0.3.

2.3. Example 2

5.0 g of hyaluronic acid (average molecular weight:3,000, manufactured by Kewpie Corporation) having the content of hyaluronic acid of 91.1% was dissolved in 500 mL of water, and the pH of the process solution was adjusted to 1.0 with hydrochloric acid. Next, ten liters of ethanol was added little by little to the process solution while stirring to separate suspension phase from supernatant phase. Further, the pH of the process solution was adjusted to 5.0 with sodium hydrate to precipitate hyaluronic acid, and the precipitation was collected by filtration and was washed three times with 100 mL of 80% (v/v) ethanol. The obtained precipitate was dried in a vacuum at 60° C. to obtain a purified hyaluronic acid.

The average molecular weight of the purified hyaluronic acid obtained in Example 2 was 3,000, and the content of hyaluronic acid in the purified hyaluronic acid was 97.1%.

2.4. Test Example 1

Purified hyaluronic acids (No.1 to 18, and No.3 corresponds to the purified hyaluronic acid obtained in Example 2) were manufactured in accordance with the same method as the method described in Example 2, except hyaluronic acids having the molecular weights shown in Table 1 were used as raw materials, as well as the pH of the process solution before adding ethanol and the pH of the process solution d before precipitation was adjusted to the values shown in Table 1. Also, the pH adjustment of the process solution was performed with hydrochloric acid or sodium hydrate.

Further, the content of hyaluronic acid in each purified hyaluronic acid of No.1 to 5, No.8 to 12, and No.15 to 17 was 95% or more, and in each case, precipitation was generated, and the average molecular weight of each purified hyaluronic acid remained unchanged from each raw material hyaluronic acid.

As for the purified hyaluronic acids of No. 1 to 18, the condition of the each process solution after the addition of the water-soluble organic medium and the condition of the each process solution after the pH adjustment were evaluated in accordance with the following criterion.

A: Suspension phase and supernatant phase were separated after the addition of the water-soluble organic medium, and precipitate was generated after pH adjustment.
B1: Suspension phase and supernatant phase were separated after the addition of the water-soluble organic medium, it was slightly difficult to precipitate at first, but, precipitate was uneventfully generated after pH adjustment.
C1: Suspension phase and supernatant phase were not separated after the addition of the water-soluble organic medium, and precipitate was not generated after pH adjustment.
B2: Suspension phase and supernatant phase were separated after the addition of the water-soluble organic medium, the process solution slightly gelated, precipitation did not smoothly proceed at first, but precipitate was uneventfully generated after pH adjustment.
C2: Suspension phase and supernatant phase were not separated after the addition of the water-soluble organic medium, the process solution gelated, and precipitate was not generated after pH adjustment.
C3: Suspension phase and supernatant phase were separated soon after the addition of the water-soluble organic medium, but precipitate was not generated after pH adjustment.

TABLE 1

| No. | Average Molecular Weight of Raw Material Hyaluronic Acid | pH of Process Solution before adding ethanol | pH of Process Solution before precipitation | condition of Process Solution |
| --- | --- | --- | --- | --- |
| 1 | 3,000 | 0.1 | 5.0 | A |
| 2 | 3,000 | 0.5 | 5.0 | A |
| 3 | 3,000 | 1.0 | 5.0 | A |
| 4 | 3,000 | 2.0 | 5.0 | A |
| 5 | 3,000 | 3.0 | 5.0 | B1 |
| 6 | 3,000 | 4.0 | 5.0 | C1 |
| 7 | 3,000 | 6.0 | 5.0 | C1 |
| 8 | 1,000 | 2.0 | 5.0 | A |
| 9 | 10,000 | 2.0 | 5.0 | A |
| 10 | 20,000 | 2.0 | 5.0 | A |
| 11 | 50,000 | 2.0 | 5.0 | A |
| 12 | 100,000 | 2.0 | 5.0 | B2 |
| 13 | 100,000 | 4.0 | 5.0 | C2 |
| 14 | 300,000 | 2.0 | 5.0 | C2 |
| 15 | 3,000 | 1.0 | 7.0 | A |
| 16 | 3,000 | 1.0 | 4.0 | A |
| 17 | 3,000 | 1.0 | 3.5 | B1 |
| 18 | 3,000 | 1.0 | 3.0 | C3 |

2.5. Example 3

Purified hyaluronic acid was manufactured in accordance with the same method as the method described in Example 1, except acetone was added in place of ethanol, which was added after cooling the reaction solution in the method of producing the purified hyaluronic acid of Example 1.

The average molecular weight of the purified hyaluronic acid obtained in Example 3 was 8,000, and the content of hyaluronic acid in the purified hyaluronic acid was 96.0%.

2.6. Example 4

Purified hyaluronic acid was manufactured in accordance with the same method as the method described in Example 2, except 1% saline solution was used in place of water, which was used for dissolving the raw material hyaluronic acid in the method of producing the purified hyaluronic acid of Example 2.

The average molecular weight of the purified hyaluronic acid obtained in Example 4 was 3,000, and the content of hyaluronic acid in the purified hyaluronic acid was 94.0%.

2.7. Example 5

Purified hyaluronic acid was manufactured in accordance with the same method as the method described in Example 2, except 2% saline solution was used in place of water, which was used for dissolving the raw material hyaluronic acid in the method of producing the purified hyaluronic acid of Example 2. Note that sodium chloride concentration of each process solution before adding ethanol in Examples 1 to 3 was less than 1%.

The average molecular weight of the purified hyaluronic acid obtained in Example 5 was 3,000, and the content of hyaluronic acid in the purified hyaluronic acid was 91.9%.

2.8. Example 6

20 g of sodium hyaluronate (average molecular weight:8, 000, manufactured by Kewpie Corporation), 20 mL of 5% sodium hydrate, 180 mL of water, and 30 mL of glycidyl trimethyl ammonium chloride (GTA (active component: about 80%, water content: about 20%)) were added to a beaker having one liter of volume, and reaction was performed for one hour at 40° C. while stirring with a magnet.

After the reaction completed, the pH of the process solution was adjusted to 1.0 with hydrochloric acid. Next, 800 mL of ethanol was added little by little while stirring to separate suspension phase from supernatant phase. Further, the pH of the process solution was adjusted to 4.0 with sodium hydrate to precipitate cationized hyaluronic acid, and then the precipitate was collected by filtration, and was washed three times with 500 mL of 80% ethanol. The obtained precipitate was dried in a vacuum at 60° C. to obtain a purified cationized hyaluronic acid.

The average molecular weight of the purified cationized hyaluronic acid obtained in Example 6 was 6,000, and the content of hyaluronic acid in the purified cationized hyaluronic acid was 95.6%.

The embodiment of the invention has been explained as set out above. The invention includes substantially the same component as a component explained in the embodiment (for example, a component having the same function, the same method, and the same result, or a component having the same object and the same result). Also, the invention includes a component, a non-essential part explained in the embodiment of which is replaced with others. Additionally, the invention includes a component having the same effect as a component explained in the embodiment, or a component which can achieve the same object as a component explained in the embodiment. Further, the invention includes a component obtained by adding a heretofore known technology to a component explained in the embodiment.

The invention claimed is:

1. A method of producing at least one selected from the group consisting of a purified hyaluronic acid, a purified cationized hyaluronic acid, and a purified salt thereof comprising:
    adding a C1—C3 aliphatic alcohol or acetone to a solution which comprises at least one selected from the group consisting of a hyaluronic acid, a cationized hyaluronic acid, and a salt thereof having an average molecular weight of 400 to 20,000 Dalton and has a pH of 3 or less to obtain a suspension; and
    adjusting the pH of the suspension in a range of 3.5 to 8 to precipitate at least one selected from the group consisting of the purified hyaluronic acid, the purified cationized hyaluronic acid, and the purified salt thereof.

2. The method of claim 1, wherein the pH of the solution before adding the C1—C3 aliphatic alcohol or acetone is 2 or less.

* * * * *